United States Patent [19]

Coulson

[11] Patent Number: 5,112,599
[45] Date of Patent: May 12, 1992

[54] ORAL COMPOSITIONS

[75] Inventor: Bryony E. Coulson, Port Sunlight, Great Britain

[73] Assignee: Chesebrough-Pond's USA Co., Division of Conopco, Inc., Greenwich, Conn.

[21] Appl. No.: 620,502

[22] Filed: Nov. 30, 1990

[30] Foreign Application Priority Data

Nov. 30, 1989 [GB] United Kingdom ............... 8927073

[51] Int. Cl.⁵ .................... A61K 7/16; A61K 7/18
[52] U.S. Cl. ........................................ 424/52; 424/57
[58] Field of Search .................................. 424/52, 57

[56] References Cited

U.S. PATENT DOCUMENTS

| | | | |
|---|---|---|---|
| 4,327,079 | 4/1982 | Aoki | 424/57 |
| 4,342,741 | 8/1982 | Aoki | 424/57 |
| 4,684,518 | 8/1987 | Parran, Jr. et al. | 424/52 |
| 4,933,171 | 6/1990 | Bristow et al. | 424/57 |
| 4,933,173 | 6/1990 | Bristow et al. | 424/54 |
| 4,988,499 | 1/1991 | Bristow et al. | 424/52 |

FOREIGN PATENT DOCUMENTS 0342380 11/1989 European Pat. Off. .
0342746 11/1989 European Pat. Off. .
2206049 12/1988 United Kingdom .

OTHER PUBLICATIONS

European Search Report and Annex.

*Primary Examiner*—Shep K. Rose
*Attorney, Agent, or Firm*—Milton L. Honig

[57] ABSTRACT

The present invention relates to oral compositions such as dentifrices which contain hydroxyapatite as abrasive material. The compatibility of hydroxyapatite with fluorine-containing anti-caries agents is improved by providing a pH of the oral compositions of between 7.0 and 11.0.

1 Claim, No Drawings

ORAL COMPOSITIONS

FIELD OF THE INVENTION

This invention relates to oral compositions. more particularly compositions for combating dental caries.

BACKGROUND OF THE INVENTION

It has long been known to include fluorine-containing compounds in dentifrices as anti-caries agents, and it has been established that these compounds are effective to reduce the incidence of dental caries. Those compounds most commonly used today are sodium fluoride and sodium monofluorophosphate. Other examples of known fluorine-containing anti-caries agents are stannous fluoride, amine fluorides and other fluoride-ion sources e.g. as described in U.S. Pat. No. 4,684,518 (Parran et al.).

In the formulation of so-called fluoride dentifrices it is recognised by those skilled in the art that during the period of time between manufacture of the dentifrice and use by the consumer, there must be no undue loss of availability of the fluoride active component due to reaction with other ingredients of the dentifrice. Of particular importance in this respect is the choice of a particulate abrasive component. Substantial loss of available fluoride through interaction with the abrasive must be avoided if the dentifrice is to be effective in inhibiting dental caries. A number of particulate abrasive agents are known to those skilled in the art to be compatible with selected fluoridating agents.

In our co-pending application EP 89201202.2 we have described that dentifrices can be formulated comprising particulate hydroxyapatite and a fluorine-containing anti-caries agent, particularly sodium fluoride or sodium monofluorophosphate in which these ingredients are compatible to a surprising extent. Although there is some loss of available fluoride upon storage, these dentifrices remain particularly suitable against dental caries.

SUMMARY OF THE INVENTION

We have now found that this loss of available fluoride in these systems can be further reduced by providing that the interaction between the hydroxyapatite and the fluoride takes place at a pH within the range of 7.0–11.0, preferably of 7.3–10.1. A particularly preferred pH range is 7.5–8.5. This can be achieved by adjusting and optionally buffering the pH of the dentifrice composition to a value within the above range.

The hydroxyapatite abrasive is used in a particle size giving satisfactory cleaning without being harmful to the tooth surface when used in appropriate amounts in dentifrices of the invention.

DETAILED DESCRIPTION

The amount of the hydroxyapatite present in oral compositions of this invention will range from 1–50%, usually from about 2% to about 20%, preferably 3 to 15%, by weight of the oral composition. It desirably has an average particle size of from about 1 to about 15 microns, usually from 2–10 and preferably 3 to 10 microns.

Preferred particulate hydroxyapatites for use in sodium fluoride- or sodium monofluorophosphate-containing dentifrices of this invention are synthetic hydroxyapatites of high purity consisting of at least 92% of $Ca_{10}(PO_4)_6(OH)_2$. The remainder will comprise mainly bound water (typically 6% maximum) and a minor amount of calcium carbonate (typically 2% maximum). A process for the preparation of hydroxyapatites is described in GB-A-1 586 915 (British Charcoals & Macdonalds).

A highly pure synthetic hydroxyapatite available commercially is that sold under the trade name CAPTAL by British Charcoals & Macdonalds of Greenock, Scotland. This contains about 97% $Ca_{10}(PO_4)_6(OH)_2$. The remaining 3% is mostly bound water with approximately 0.3% calcium carbonate.

The sodium monofluorophosphate will generally be present in the dentifrices of this invention in an amount sufficient to provide from about 50 ppm to about 5000 ppm F, especially from 200 ppm to 1500 ppm and more especially from 500 ppm to 1500 ppm.

The oral composition of this invention will, of course, also contain other ingredients commonly used to formulate such products, depending on the form of the oral product. For instance, in the case of an oral product in the form of a dentifrice cream or paste the product will comprise an humectant-containing liquid phase and a binder or thickener which acts to maintain the particulate solid abrasive in stable suspension in the liquid phase. A surfactant and a flavouring agent are also usual ingredients of commercially acceptable dentifrices.

Humectants commonly used are glycerol and sorbitol syrup (usually comprising an approximately 70% solution). However, other humectants are known to those in the art including propylene glycol, lactitol, and hydrogenated corn syrup. The amount of humectant will generally range from about 10 to 85% by weight of the dentifrice. The liquid phase can be aqueous or nonaqueous.

Likewise numerous binding or thickening agents have been indicated for use in dentifrices, preferred ones being sodium carboxymethylcellulose and xanthan gum. Others include natural gum binders such as gum tragacanth, gum karaya and gum arabic, Irish moss, alginates and carrageenans. Silica thickening agents include the silica aerogels and various precipitated silicas. Mixtures of binders may be used. The amount of binder included in a dentifrice is generally between 0.1 and 10% by weight.

It is usual to include a surfactant in a dentifrice and again the literature discloses a wide variety of suitable materials. Surfactants which have found wide use in practice are sodium lauryl sulphate, sodium dodecylbenzene sulphonate and sodium lauroylsarcosinate. Other anionic surfactants may be used as well as other types such cationic, amphoteric and non-ionic surfactants. Surfactants are usually present in an amount of from 0.5 to 5% by weight of the dentifrice.

Flavours that are usually used in dentifrices are those based on oils of spearmint and peppermint. Examples of other flavouring materials used are menthol, clove, wintergreen, eucalyptus and aniseed. An amount of from 0.1% to 5% by weight is a suitable amount of flavour to incorporate in a dentifrice.

The oral compositions of the invention may also comprise a proportion of a supplementary abrasive agent such as silica, alumina, hydrated alumina, calcium carbonate, anhydrous dicalcium phosphate, dicalcium phosphate dihydrate and water-insoluble sodium metaphosphate.

The oral composition of the invention may include a wide variety of optional ingredients. These include an anti-plaque agent such as an antimicrobial compound for example chlorhexidine or 2,4,4'-trichloro-2'-hydroxydiphenyl ether, or a zinc salt (see EP-A-161 898); an anti-tartar ingredient such as a condensed phosphate e.g. an alkali metal pyrophosphate, hexametaphosphate or polyphoshate, (see U.S. Pat. No. 4,515,772 and U.S. Pat. No. 4,627,977) or zinc citrate (see U.S. Pat. No. 4,100,269); sweetening agent such as saccharin; an opacifying agent, such as titanium dioxide; a preservative, such as formalin, or a colouring agent.

For a fuller discussion of the formulation of oral composition reference is made to Harry's Cosmeticology, Seventh Edition, 1982, Edited by J. B. Wilkinson and R. J. Moore, pages 609 to 617.

The invention also relates to a method of combating dental caries which consists in applying to the teeth, such as by brushing, an oral composition according to the invention.

The invention is further illustrated by the following Examples. Percentage and parts are by weight.

EXAMPLE 1

Model systems were made comprising 10% Captal 3 (average particle size 8 microns) and 0.76% sodium monofluorophosphate (SMFP), the balance being water.

The stability of the fluoride in these systems at various pH's was evaluated by determining water extractable fluoride (WEF) values. These values were obtained by filtering to remove the solid components, diluting the supernatant (1 part supernatant with 99 parts water), hydrolysing the SMFP and then analysing the supernatant for fluoride with a fluoride electrode.

The following Table shows 1 month' storage stability data at room temperature for the systems which had an initial nominal fluoride content of 1000 ppm.

TABLE

| | Total flouride in Supernatant | | | | | |
|---|---|---|---|---|---|---|
| | System | | | | | |
| | Initial after manufacture | | After 1 month | | After 3 months | |
| | pH | % residual F | pH | % residual F | pH | % residual F |
| 1000 ppm F as SMFP | 6.6 | 100 | 6.7 | 98 | 6.6 | 76 |
| id. + Captal | 5.0 | 90 | 5.1 | 58 | 5.3 | 31 |
| id. + Captal | 6.7 | 97 | 6.8 | 77 | 6.8 | 51 |
| id. + Captal | 8.0 | 100 | 7.5 | 86 | 7.4 | 67 |
| id. + Captal | 11.0 | 100 | 11.0 | 89 | 10.5 | 63 |

EXAMPLE 2

The following toothpaste formulations were made:

| | Control pH 6 | A pH 7 | B pH 8 (buffered) |
|---|---|---|---|
| pH after 3 months | | | |
| CAPTAL #3 | 10.00 | 10.00 | 10.00 |
| Precipitated silica | 10.00 | 10.00 | 10.00 |
| Sorbitol (70%) | 45.00 | 45.00 | 45.00 |
| Xanthan gum | 1.10 | 1.10 | 1.10 |
| Sodium Lauryl Sulphate | 1.50 | 1.50 | 1.50 |
| Saccharin | 0.20 | 0.20 | 0.20 |
| Titanium dioxide | 1.00 | 1.00 | 1.00 |
| Flavour | 1.00 | 1.00 | 1.00 |
| Formalin | 0.04 | 0.04 | 0.04 |
| Sodium monofluorophosphate | 0.82 | 0.82 | 0.82 |
| Sodium hydroxide | — | 0.15 | 0.15 |
| Trisodium orthophosphate | — | — | 0.15 |
| Water to 100% | | | |

The residual fluoride after storage was determined, and the results are given below:

| | Control | A | B |
|---|---|---|---|
| Initial F ppm | 1000 | 1000 | 1000 |
| 1 months storage | | | |
| at 6° C.: ppm F | 877 | 900 | 961 |
| at 20° C.: ppm F | 760 | 803 | 853 |
| at 37° C.: ppm F | 484 | 600 | 573 |
| at 50° C.: ppm F | 208 | 333 | 400 |
| 3 months storage | | | |
| at 6° C.: ppm F | 736 | 754 | 960 |
| at 20° C.: ppm F | 694 | 698 | 850 |
| at 37° C.: ppm F | 403 | 398 | 564 |
| at 50° C.: ppm F | 89 | 144 | 218 |

I claim:

1. An oral composition in the form of an aqueous toothpaste for combating dental caries, comprising from about 50 to about 5,000 ppm of a fluorine-containing anti-caries agent selected from the group consisting of sodium fluoride and sodium monofluorophosphate and from about 1–50% by weight of a particulate hydroxyapatite abrasive material, said composition having a pH of between 7.5 and 8.5.

* * * * *